(12) United States Patent
Abraham et al.

(10) Patent No.: US 12,103,912 B2
(45) Date of Patent: *Oct. 1, 2024

(54) METHODS FOR PRODUCING ALKYL HYDROXYALKANOATES

(71) Applicant: CARGILL, INCORPORATED, Wayzata, MN (US)

(72) Inventors: Timothy Walter Abraham, Minnetonka, MN (US); Ravi R. Gokarn, Omaha, NE (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/663,071

(22) Filed: May 12, 2022

(65) Prior Publication Data
US 2022/0267245 A1  Aug. 25, 2022

Related U.S. Application Data

(63) Continuation of application No. 16/270,143, filed on Feb. 7, 2019, now Pat. No. 11,332,428, which is a continuation of application No. 15/926,575, filed on Mar. 20, 2018, now Pat. No. 10,207,979, which is a continuation of application No. 15/029,357, filed as application No. PCT/US2014/061192 on Oct. 17, 2014, now Pat. No. 9,938,224.

(60) Provisional application No. 61/892,126, filed on Oct. 17, 2013.

(51) Int. Cl.
*C07C 67/08* (2006.01)
*C07C 67/03* (2006.01)
*C07C 67/54* (2006.01)

(52) U.S. Cl.
CPC .............. *C07C 67/08* (2013.01); *C07C 67/03* (2013.01); *C07C 67/54* (2013.01)

(58) Field of Classification Search
CPC .......... C07C 67/08; C07C 67/54; C07C 67/03
See application file for complete search history.

(56) References Cited

U.S. PATENT DOCUMENTS

| 2,379,625 A | 7/1945 | Coes, Jr. |
| 2,469,701 A | 5/1949 | Redmon |
| 2,859,240 A | 11/1958 | Holmen |

(Continued)

FOREIGN PATENT DOCUMENTS

| DE | 3222837 A1 | 12/1983 |
| GB | 744582 A | 2/1956 |

(Continued)

OTHER PUBLICATIONS

"Aldrich Chemical Co., Inc.,", Catalog, p. 961 (1996).
(Continued)

*Primary Examiner* — Deborah D Carr

(57) ABSTRACT

Methods and systems for producing alkyl hydroxyalkanoate from hydroxycarboxylic acid recovery bottoms. The methods generally comprise the steps of obtaining a hydroxycarboxylic acid recovery bottom, adding a mono-alcohol to the hydroxycarboxylic acid recovery bottom to obtain a first mixture, heating the first mixture, optionally in the presence of a catalyst, to form a reaction product, distilling the reaction product, and recovering an alkyl hydroxyalkanoate fraction.

20 Claims, 1 Drawing Sheet

(56) References Cited

U.S. PATENT DOCUMENTS

Figure 1:
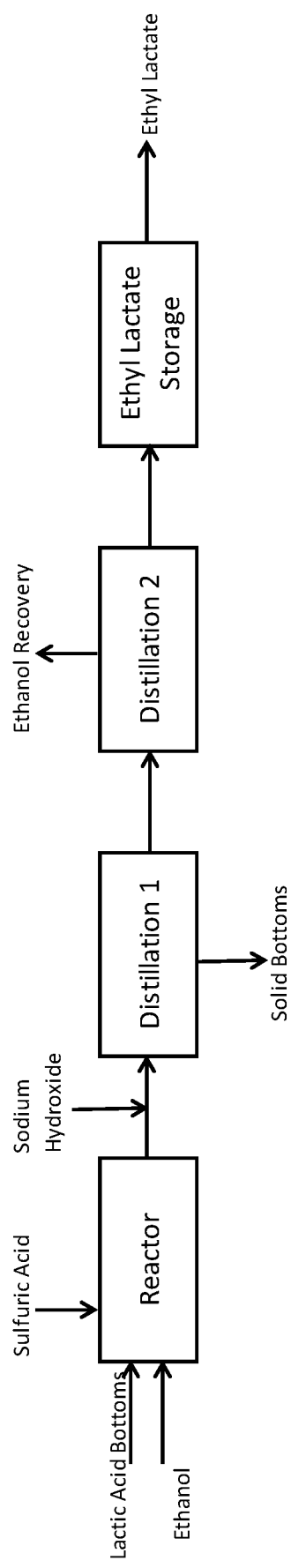

| | | |
|---|---|---|
| 3,590,073 A | 6/1971 | Carr |
| 3,619,397 A | 11/1971 | Jacquemet |
| 3,639,466 A | 2/1972 | Leichtle |
| 3,699,059 A | 10/1972 | Smeets |
| 3,875,212 A | 4/1975 | Ohrui |
| 3,954,854 A | 5/1976 | Gehrmann |
| 4,187,300 A | 2/1980 | Kinnamon |
| 4,211,846 A | 7/1980 | Lafferty |
| 4,729,978 A | 3/1988 | Sawicki |
| 4,786,756 A | 11/1988 | Paparizos |
| 4,792,620 A | 12/1988 | Paulik |
| 4,937,359 A | 6/1990 | Seebach |
| 4,970,334 A | 11/1990 | Argyropoulos |
| 5,132,456 A | 7/1992 | King |
| 5,210,296 A | 5/1993 | Cockrem |
| 5,294,720 A | 3/1994 | Jadhav |
| 5,371,273 A | 12/1994 | Shima |
| 5,439,674 A | 8/1995 | Noda |
| 5,659,029 A | 8/1997 | Ellis, Jr. |
| 5,739,379 A | 4/1998 | Shima |
| 6,452,051 B1 | 9/2002 | Eyal |
| 6,803,217 B2 | 10/2004 | Moore |
| 6,902,917 B1 | 6/2005 | Moore |
| RE39,333 E | 10/2006 | Nishiyama |
| 7,186,541 B2 | 3/2007 | Gokarn |
| 7,297,809 B2 | 11/2007 | Martino-Gauchi |
| 7,652,167 B2 * | 1/2010 | Miller ............... B01D 3/009 560/179 |
| 7,737,296 B2 | 6/2010 | Kozono |
| 7,999,130 B2 | 8/2011 | Ackermann |
| 8,338,145 B2 | 12/2012 | Tsobanakis |
| 9,012,685 B2 | 4/2015 | Hwang |
| 9,938,224 B2 | 4/2018 | Abraham |
| 9,944,586 B2 | 4/2018 | Abraham |
| 10,207,979 B2 | 2/2019 | Abraham |
| 10,301,249 B2 | 5/2019 | Abraham |
| 2001/0008736 A1 | 7/2001 | Fanta |
| 2002/0055650 A1 | 5/2002 | Hidaka |
| 2004/0210087 A1 | 10/2004 | Meng |
| 2005/0221457 A1 | 10/2005 | Tsobanakis |
| 2005/0222456 A1 | 10/2005 | Brands |
| 2005/0222458 A1 | 10/2005 | Craciun |
| 2006/0041165 A1 | 2/2006 | Tretjak |
| 2007/0191629 A1 | 8/2007 | Chen |
| 2009/0298144 A1 | 12/2009 | Tsobanakis |
| 2010/0113822 A1 | 5/2010 | Craciun |
| 2010/0273224 A1 | 10/2010 | Joachim |
| 2011/0125118 A1 | 5/2011 | Lynch |
| 2011/0160480 A1 | 6/2011 | Hottois |
| 2012/0142945 A1 | 6/2012 | Hwang |
| 2013/0150616 A1 | 6/2013 | Tsobanakis |
| 2013/0281649 A1 | 10/2013 | Yoshida |
| 2013/0345470 A1 | 12/2013 | Tengler |
| 2016/0229787 A1 | 8/2016 | Abraham |
| 2016/0272569 A1 | 9/2016 | Abraham |

FOREIGN PATENT DOCUMENTS

| | | |
|---|---|---|
| GB | 1082179 A | 9/1967 |
| JP | 146815 C | 11/1941 |
| JP | 52108088 A | 9/1977 |
| JP | 5318794 A | 2/1978 |
| JP | 56021593 | 2/1981 |
| JP | 58158189 A | 9/1983 |
| JP | 6078941 A | 5/1985 |
| JP | 63188650 A | 8/1988 |
| JP | 63313739 A | 12/1988 |
| JP | 03264551 A | 11/1991 |
| JP | 05336981 A | 12/1993 |
| JP | 0717909 A | 1/1995 |
| JP | 09132555 A | 5/1997 |
| JP | 09143126 A | 6/1997 |
| JP | 1072401 A | 3/1998 |
| JP | 2000319227 A | 11/2000 |
| JP | 2002053524 A | 2/2002 |
| WO | 0116346 W | 3/2001 |
| WO | 02090312 W | 11/2002 |
| WO | 2003082795 A2 | 10/2003 |
| WO | 2013134385 A1 | 9/2013 |
| WO | 2015058116 A1 | 4/2015 |
| WO | 2015058118 A1 | 4/2015 |
| WO | 2016061356 A1 | 4/2016 |

OTHER PUBLICATIONS

"Classification Table of Catalysts for Reactions, published by Kagaku Kogyo, edited by Taruma Lab, Kyoto University", ISDN: 3058-09019-0915, 173-178.

"English abstract for JP63313739 downloaded from Derwent on Apr. 20, 2009".

"Industrial Catalytic Reaction I, edited by Kodansha Scientific, Published by Kodansha Ltd.", ISBN: 4-06-191408-1(0), 9 page.

Bartoli, et al., "An Efficient Procedure for the Diastereoselective Dehydration of β-Hydroxy Carbonyl Compounds by CeCl 3—7H 2 O/NaI System", Organic Letters, vol. 2, No. 13, 2000, 1791-1793.

Chattopadhyay, et al., "Enzymatic Esterfication of 3-Hydroxybutyric Acid", Biotechnology Letters, vol. 15, Issue 3, Mar. 1993, 245-250.

D. Pressman and H. J. Lucas, "Hydration of Unsaturated Compound XI. Acrolein and Acrylic Acid", Journal of the American Chemical Society, Aug. 1942, 1953-1957.

Hasegawa, et al., "Production of beta-Hydroxypropionic Acid from Propionic Acid", Journal of Fermentation Technology, vol. 60, No. 6, Dec. 1982, 591-594.

Kissa, et al., "Solubility of Alkali Metal Carboxylates in Hydrocarbons", Journal of Colloid Science, vol. 17, No. 9, Dec. 1962, 857-864.

Kumar et al. (Biotechnology Advances, Recent advances in biological production of 3-hydroxypropionic acid, 2013, 31, pp. 945-961) (Year: 2013).

Levene, et al., "The Configurational Relationships of 2-Hydroxy, 3-Hydroxy and 4-Hydroxy Acids", Journal of Biological Chemistry, vol. 69, Apr. 1926, 165-173.

Lira, et al., Conversion of Lactic Acid to Acrylic Acid in Near-Critical Water, "Ind. Eng. Chem. Res.(1993) 32: 02608-2613".

Mats From, et al., "Lipase catalyzed esterification of lactic acid", Biotechnology Letters, vol. 19, Issue 4, Apr. 1997, 315-318.

Morrison, et al., "Organic Chemistry", vol. 1, Fourth edition, 1983,, 423 Pages.

Odell, et al., "Hydrothermal reactions of lactic acid catalysed by group: VIII Metal complexes", Journal of Organometallic Chemistry, vol. 290, Issue 2, Jul. 23, 1985, 241-248.

Riemenschneider, et al., "Ullmann's Encyclopedia of Industrial Chemistry", Sixth Edition, 1999 Electronic Release, 1999, Wiley-VCH, Weinheim, Germany, XP002247378 Esters, Organic-Production.

Seo, et al., "Kinetics of Esterification of Lactic Acid with Methanol in the Presence of Cation Exchange Resin Using a Pseudo-Homogeneous Model", Journal of Chemical Engineering of Japan, vol. 33, No. 1, (2000)., 2000, pp. 128-133.

Shahid et al., Journal of Bioscience and Bioengineering, Impact of carbon source and variable nitrogen conditions on bacterial biosynthesis of polyhydroxyalkonates: Evidence of an atypical metabolism in Bacillus megaterium DSM 509, 2013, 116(3), pp. 302-308.

Sharma, et al., Enantio-reversal in Candida rugosa lipase-catalyzed esterification of 3-hydroxybutyric acid, "Journal of Molecular Catalysis B: Enzymatic, 10(5)", 531-534.

Van Der Baan, et al., "Synthesis of β-Hydroxy Esters by Lithium/ Ammonia Rejection of a, β-Epoxy Esters", Synthesis, vol. 10, Oct. 1990, 897-899.

W.A. Drushel, et al., "On the Preparation and Hydrolysis of Ethyl Hydracrylate", American Journal of Science, vol. 39, 1915, 113-121.

Zaragoza, Dorwald, Side Reactions in Organic Synthesis, 2005, Whiley-VCH Verlag Gmbh & Co. KGaA, Weinheim, Preface. p. 1X.

(56) References Cited

OTHER PUBLICATIONS

Fischer, Emil, "Zur Kenntnis der Waldenschen Umkehrung IV," Chemische Berichte, 42, pp. 1219-1228 (Mar. 1909), XP001149222 Verlag Chemie GMBH, Weinheim, DE ISSN: 0009-2940, p. 1121, paragraph 3.

* cited by examiner

METHODS FOR PRODUCING ALKYL HYDROXYALKANOATES

CROSS-REFERENCE TO RELATED APPLICATIONS

This application is a Continuation of U.S. patent application Ser. No. 16/270,143, filed Feb. 7, 2019, which is a Continuation of U.S. Pat. No. 10,207,979, issued Feb. 19, 2019, which is a Continuation of U.S. Pat. No. 9,938,224, issued Apr. 10, 2018, which is a national phase application of PCT/US2014/061192, filed Oct. 17, 2014, which claims the benefit of the U.S. Provisional Patent Application No. 61/892,126, filed Oct. 17, 2013, each of which is hereby incorporated by reference in its entirety.

TECHNICAL FIELD

The present disclosure generally relates to methods and systems for producing alkyl hydroxyalkanoates from hydroxy alkanoate recovery bottoms.

BACKGROUND

During the production and purification process of a hydroxycarboxylic acid, for example lactic acid, the hydroxycarboxylic acid is evaporated or distilled from less-volatile compounds present in a partially purified fermentation broth. These less-volatile components, which contain significant amounts of hydroxycarboxylic acid in the form of oligomers of hydroxycarboxylic acid and saccharide esters, are purged out of the system as waste, which incurs a significant yield loss, as well as solid waste disposal costs. Thus, it is desirable to turn such waste streams into something having economic benefit.

SUMMARY

Provided herein are methods for producing an alkyl hydroxyalkanoate, comprising obtaining a hydroxyalkanoate containing composition, comprising at least 40 percent by weight hydroxyalkanoate equivalents, less than 45 percent by weight free hydroxyalkanoates, at least 1 percent by weight saccharide equivalents, and less than 15 percent by weight water; mixing a mono-alcohol in a molar ratio of from about 1.1 to 1.0 to about 10.0 to 1.0 of mono-alcohol to hydroxyalkanoate equivalents present in the hydroxyalkanoate containing composition to obtain a first mixture; heating the first mixture in the presence of a catalyst to form a reaction product; and distilling the reaction product and recovering an alkyl hydroxyalkanoate fraction comprising at least 90 percent by weight alkyl hydroxyalkanoate, less than 1 percent by weight hydroxyalkanoic acid, less than 1 percent by weight water; and less than 0.5 percent by weight saccharide equivalents.

In the above embodiments, the hydroxyalkanoate typically comprises an alpha-, beta-, or gamma-hydroxyalkanoate, for example 2-hydroxypropionic acid (i.e., lactic acid) or 3-hydroxypropionic acid, preferably 2-hydroxypropionic acid. Typically, the mono-alcohol comprises methanol, ethanol, propanol, or butanol (for example, methanol or ethanol, and preferably ethanol). Preferably, the alkyl hydroxyalkanoate comprises methyl, ethyl, propyl, or butyl hydroxypropionate, more preferably, ethyl lactate or ethyl 3-hydroxypropionate.

FIGURES

Figure 2:
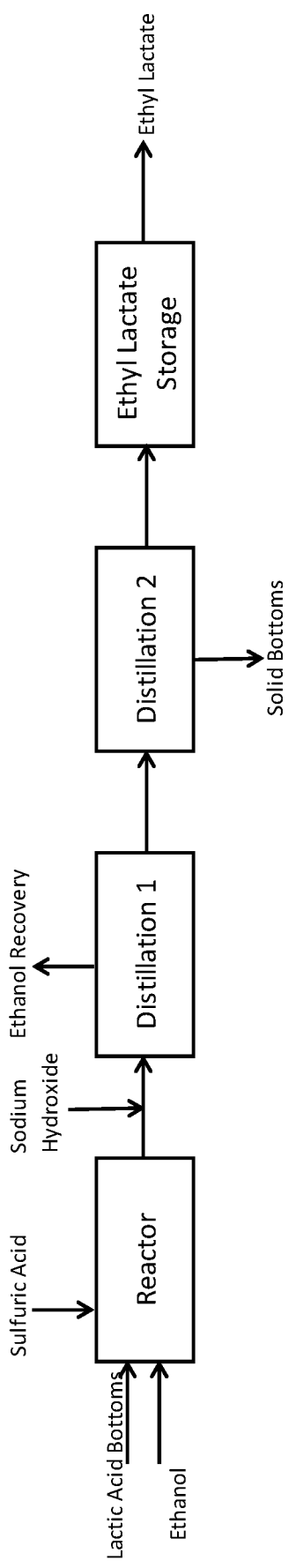

FIGS. 1 and 2 illustrate an exemplary flow diagram for methods of producing ethyl lactate from lactic acid recovery bottoms.

DETAILED DESCRIPTION

"Free hydroxyalkanoate" is measured and determined using similar methods as those described for analyzing and determining free acidity in Holten, C. H. *Lactic Acid—Properties and Chemistry of Lactic Acid and Derivatives*, Verlag Chemie (1971): pp. 199-203. An example calculation of free hydroxyalkanaote (i.e., free hydroxyprionate) is set forth in the examples below. Free hydroxyalkanoate is indicative of the monomeric 2, 3, 4, and 5 carbon hydroxyalkanoic acid (i.e., hydroxycarboxylic acid), monomeric 2, 3, 4, and 5 carbon hydroxyalkanoate salts, and combinations thereof, but not hydroxyalkanoate esters in a material being measured.

"Free hydroxypropionate" is indicative of the monomeric 3 carbon hydroxypropionic acid, monomeric 3 carbon hydroxypropionate salts, and combinations thereof, but not hydroxypropionate esters in a material being measured. It is measured based on the method described for free hydroxyalkanaote.

"Hydroxyalkanoate containing composition" is defined as a mixture of oligomers and esters of hydroxyalkanoate, for example esters with saccharides, with optionally monomeric hydroxyalkanoates, and water. It is typically derived from hydroxycarboxylic acid recovery bottom streams, but may come from other sources as well.

"Hydroxyalkanoate equivalents" is measured and determined using similar methods as those described for analyzing and determining total lactic (adjusted to account for all esters and expressed as free hydroxalkanoic acid basis) in Holten, C. H. *Lactic Acid—Properties and Chemistry of Lactic Acid and Derivatives*, Verlag Chemie (1971): pp. 199-203. The esters of hydroxyalkanoate with themselves and saccharides will be hydrolyzed in a similar manner to enable ready calculation of hydroxyalkanoate equivalents. An example calculation of hydroxyalkanoate equivalents (e.g., hydroxypropionate equivalents) is set forth in the examples below. Hydroxyalkanoate equivalents is indicative of the monomeric equivalents in the hydroxyalkanoate containing composition whether in the form of monomers, oligomers, and/or esters with other compounds such as saccharides. For example, a dimeric hydroxyalkanoate contains two hydroxyalkanoate equivalents. As another example, a trimeric hydroxyalkanoate contains three hydroxyalkanoate equivalents. As another example, a saccharide esterified with one hydroxyalkanoate contains one hydroxyalkanoate equivalent, and a saccharide esterified with two hydroxyalkanoate groups contains two hydroxyalkanoate equivalents.

"Hydroxypropionate containing composition" is defined as a mixture of oligomers and esters of hydroxypropionate, for example esters with saccharides, with optionally monomeric hydroxypropionates and water. It is typically derived from lactic acid or 3-hydroxypropionic (3-HP) recovery bottom streams, but may come from other sources as well.

"Hydroxypropionate equivalents" is defined as a measure of the monomeric equivalents in the hydroxypropionate containing composition whether in the form of monomers, oligomers, and/or esters with other compounds such as saccharides. For example, a dimeric hydroxypropionate contains two hydroxypropionate equivalents. As another example, a trimeric hydroxypropionate contains three hydroxypropionate equivalents. As another example, a saccharide esterified with one hydroxypropionate contains one hydroxypropionate equivalent, and a saccharide esterified with two hydroxypropionate groups contains two hydroxyalkanoate equivalents. It is measured based on the method described for hydroxyalkana\te equivalents.

"Overall recovery" is defined as the moles of alkyl hydroxyalkanoate recovered at the end of the process divided by the moles of hydroxyalkanoate equivalents in the hydroxyalkanoate containing composition, multiplied by one hundred.

"Percent recovery" is defined as the moles of alkyl hydroxyalkanoate recovered at the end of the process divided by the moles of alkyl hydroxyalkanoate in the reaction product, multiplied by one hundred.

"Percent yield" is defined as the moles of alkyl hydroxyalkanoate in the reaction product divided by the moles of hydroxyalkanoate equivalents in the hydroxyalkanoate containing composition, multiplied by one hundred.

"Recovery bottom" is defined as the purge fraction remaining after the recovery of prime monomeric hydroxycarboxylic acids, lactic acid, or 3-HP acid by distillation or evaporation (or other recovery methods known to one of skill in the art).

"Saccharide equivalents" is defined as a measure of the monomeric equivalents of saccharides whether in the form of monosaccharides, disaccharides, oligosaccharides, and/or esters with other compounds, such as hydroxycarboxylic acid. For example, a monosaccharide esterified with one or more hydroxycarboxylic acids contains one saccharide equivalents. A disaccharide esterified with one or more hydroxycarboxylic acids contains two saccharide equivalents. As another example, a sugar alcohol consists of one saccharide equivalent.

Producing Alkyl Hydroxyalkanoate from Hydroxycarboxylic Acid Recovery Bottoms

In one preferred embodiment, the method comprises obtaining a hydroxycarboxylic acid recovery bottom, such as the recovery bottoms obtainable from a plant manufacturing three carbon or four carbon hydroxycarboxylic acids using an evaporative or distillation-based recovery system, combining a C1 to C6 mono-alcohol with the hydroxycarboxylic acid recovery bottom to obtain a first mixture, heating the first mixture, optionally in the presence of a catalyst, to form a reaction product, distilling the reaction product and recovering an alkyl hydroxyalkanoate fraction.

In one aspect of this embodiment, the hydroxycarboxylic acid recovery bottom comprises at least 40 percent (%) by weight hydroxyalkanoate equivalents, less than 5% by weight free hydroxyalkanoates, at least 1% by weight saccharide equivalents, and less than 5% by weight water.

In another more typical aspect, the hydroxycarboxylic acid recovery bottom comprises at least 40% by weight hydroxyalkanoate equivalents (for example, at least 50%, at least 60%, at least 70%, or at least 80% by weight), greater than 0% and less than 45% by weight free hydroxyalkanoates (for example, greater than 1% and less than 40%, greater than 10% and less than 40%, or greater than 10% and less than 30%), at least 1% by weight saccharide equivalents, and less than 15% by weight water (for example less than 12%, less than 10%, less than 8%, or less than 5% by weight water). In one aspect, the hydroxyalkanoate may be hydroxypropionate, and preferably lactic acid or 3-hydroxypropionic acid.

The saccharide is typically a reducing sugar, for example, glucose, maltose, isomaltose, or combinations thereof, and may also include sugar alcohols, for example, polyols such as arabitol, glycerol, or combinations thereof.

The recovered alkyl hydroxyalkanoate fraction in this embodiment comprises at least 90% by weight alkyl hydroxyalkanoate, less than 1% by weight hydroxycarboxylic acid, less than 1% by weight water, and less than 0.5% by weight saccharide equivalents. In one aspect, the alkyl hydroxyalkanoate is alkyl hydroxypropionate, and preferably ethyl lactate.

Producing Alkyl Hydroxyalkanoate from a Hydroxyalkanoate Containing Composition

In another embodiment, the method comprises a first step of obtaining a hydroxyalkanoate containing composition. In preferred aspects, the hydroxyalkanoate containing composition is derived from recovery bottoms.

Hydroxyalkanoate Containing Composition

In one aspect, the hydroxyalkanoate containing composition comprises at least 40 percent (%) by weight of hydroxyalkanoate equivalents, less than 5% by weight free hydroxyalkanoates, at least 1% by weight saccharide equivalents, and less than 5% by weight water.

In another aspect, the hydroxyalkanoate containing composition of the present invention comprises at least 40 percent (%) by weight of hydroxyalkanoate equivalents, greater than 0% and less than 45% by weight free hydroxyalkanoates, at least 1% by weight saccharide equivalents, and less than 15% by weight water.

(i) Hydroxyalkanoate Equivalent & Free Hydroxyalkanoate

The hydroxyalkanoate equivalents present in the hydroxyalkanoate containing composition makes up at least 40% by weight of the overall hydroxyalkanoate containing composition. For example, the hydroxyalkanoate containing composition may comprise at least 50% by weight hydroxyalkanoate equivalents, at least 60% by weight hydroxyalkanoate equivalents, at least 70% by weight hydroxyalkanoate equivalents, or at least 80% by weight hydroxyalkanoate equivalents.

The free hydroxyalkanoate present in the hydroxyalkanoate containing composition makes up greater than 0% and less than 45% by weight of the overall hydroxyalkanoate composition. For example, the hydroxyalkanoate containing composition may comprise less than 40% by weight free hydroxyalkanaote, less than 35% by weight free hydroxyalkanaote, less than 30% by weight free hydroxyalkanaote, less than 25% by weight free hydroxyalkanaote, and in some aspects less than 5% by weight of the overall hydroxyalkanoate composition. In other aspects, the hydroxyalkanoate containing composition comprises less than 3% by weight of free hydroxyalkanoate, less than 2% by weight of free hydroxyalkanoate, or less than 1% by weight of free hydroxyalkanoate. Yet in other aspects, the hydroxyalkanaote containing composition comprises at least 0.1% by weight of free hydroxyalkanoate, at least 1% by weight free hydroxyalkanoate, at least 5% by weight free hydroxyalkanoate, at least 10% by weight free hydroxyalkanoate, at least 15% by weight free hydroxyalkanoate, or at least 20% by weight free hydroxyalkanoate.

In particularly preferred aspects, the amount of free hydroxyalkanaote present in the hydroxyalkanoate containing composition is greater than 1% and less than 40, and more preferably greater than 10% and less than 40, and even more preferably greater than 10% and less than 30%. Without being bound by any theory, it is believed that increasing the amount of free hydroxyalkanoate above 1% may enhance the esterification/transesterification reaction.

The hydroxyalkanoate typically comprises an alpha-, beta-, or gamma-hydroxyalkanoate, for example 2-hydroxypropionic acid (i.e., lactic acid) or 3-hydroxypropionic acid, and preferably 2-hydroxypropionic acid.

(ii) Saccharide Equivalents

The saccharide equivalents present in the hydroxyalkanoate containing composition make up at least 1% by weight of the overall hydroxyalkanoate containing composition. For example, in some aspects, the saccharide equivalents make up at least 2% by weight of the overall hydroxyalkanoate containing composition, at least 3% by weight of the overall hydroxyalkanoate containing composition, and more preferably at least 5% by weight of the overall hydroxyalkanoate containing composition.

The saccharide is typically a reducing sugar, for example, glucose, maltose, isomaltose, or combinations thereof, and may also include sugar alcohols, for example, polyols such as arabitol, glycerol, or combinations thereof.

(iii) Water

The water present in the hydroxyalkanoate containing composition makes up less than 15% by weight of the overall hydroxyalkanoate composition. For example, in some aspects, the hydroxyalkanoate containing composition comprises less than 12% by weight water, less than 10% by weight water, less than 8% by weight water, 3% by weight water, less than 2% by weight water, or preferably less than 1% by weight water.

Reacting the Hydroxyalkanoate Composition with Mono-Alcohol

For all embodiments, the mono-alcohol is typically combined with the hydroxyalkanoate containing composition. The mono-alcohol is added in a molar ratio ranging typically from 1.1 to 1.0 to 10.0 to 1.0 (for example from 1:1 to 5:1, from 1:1 to 3:1) of mono-alcohol to hydroxyalkanoate equivalents present in the hydroxyalkanoate containing composition. The resultant mixture of mono-alcohol and the hydroxyalkanoate containing composition is a first mixture.

Typically, the mono-alcohol comprises methanol, ethanol, propanol, or butanol (for example, methanol or ethanol, and preferably ethanol).

The First Mixture

For all embodiments, the first mixture is heated to form a reaction product. The first mixture is typically heated to a temperature ranging from 50 degrees Celsius (° C.) to 110° C. In alternatives, the first mixture may be heated to a temperature ranging from 50° C. to 300° C., for example from 50° C. to 275° C., from 50° C. to 250° C., or from 50° C. to 200° C. In certain aspects, the first mixture is heated to a temperature from the reflux temperature of the first mixture at a given reaction pressure to 20° C. below the reflux temperature, for example from the reflux temperature of the first mixture at a given reaction pressure to 10° C. below the reflux temperature, or from the reflux temperature of the first mixture at a given reaction pressure to 5° C. below the reflux temperature of the first mixture at the given reaction pressure.

The pressure of the first mixture during the heating step typically ranges from 0 PSIG (i.e., 1 atm) to 125 PSIG, and more preferably 50 PSIG to 125 PSIG. In alternatives, the pressure of the first mixture during the heating step may range from 1 atm. to 100 atm., more preferably from 5 atm. to 75 atm., and even more preferably from 10 atm. to 50 atm.

Optionally, a catalyst may be used to assist in the formation of the reaction product during the heating step. If a catalyst is used, typically the catalyst is an acid catalyst. More specifically, the catalyst may be a solid acid catalyst, a Bronsted acid catalyst, a Lewis acid catalyst, or combinations thereof.

In a preferred aspect, the catalyst comprises sulfuric acid, and the initial amount of catalyst present ranges from 0.01 to 5% by weight of the hydroxyalkanoate containing composition in the first mixture, and more preferably ranges from 0.1 to 3% by weight of the hydroxyalkanoate containing composition, and even more preferably ranges from 0.5 to 2% by weight of the hydroxyalkanoate containing composition.

An alternative to using a catalyst is to run the reaction in the absence of a catalyst. Without being bound by theory, it is believed that under such conditions the reaction proceeds as an autocatalyzed reaction, wherein the acid groups in the hydroxyalkanoate (e.g., lactic acid) composition are sufficient to catalyze the reaction. A particular advantage of this alternative aspect is that it significantly reduces the alkali needed for neutralization (optional neutralizing step discussed below) prior to distillation, and also reduces the water introduced by the aqueous alkali, as well as that formed during neutralization. In this alternative aspect, however, it may be necessary to run the reaction at a higher temperature and pressure (when compared to catalyzed reactions) to achieve the desired yields in a reasonable period of time.

Optional Neutralizing/pH Adjustment Step

For all embodiments, an optional neutralizing/pH adjustment step may be carried out before distillation. In this step, the pH of the acid catalyst and any free organic acids that remain in the reaction product may be adjusted using a concentrated base solution to a targeted pH value typically ranging from 3 to 7.5, for example from 4 to 6.5, or from 4 to 6. In some instances, it may be desirable to obtain a pH from 6.5 to 7.5.

Optional High Boiling Solvent Addition Step

For all embodiments, optionally, a high boiling solvent, for example but not limited to glycerol, may be added to the reaction product (after the reaction to form the first mixture), before the distillation step, to maintain the first mixture in a fluid state during the distillation.

Distilling the Reaction Product

For all embodiments, the reaction product typically is subsequently distilled. Specifically, the reaction product is distilled to recover an alkyl hydroxyalkanoate fraction. In a typical aspect, the alkyl hydroxyalkanoate fraction comprises at least 90% by weight alkyl hydroxyalkanoate, less than 1% by weight hydroxyalkanoic acid, less than 1% by weight water, and less than 0.5% by weight saccharide equivalents; and the saccharide equivalents in the alkyl hydroxyalkanoate fraction is less than 0.1% by weight or even less than 0.05% by weight.

Preferably, the alkyl hydroxyalkanoate comprises methyl, ethyl, propyl, or butyl hydroxypropionate, and more preferably ethyl lactate or ethyl 3-HP.

In a first aspect, the distillation step comprises separating the reaction product into a first fraction enriched in the mono-alcohol and water, and a second fraction, which may be in the form of distillate bottoms, enriched in the alkyl hydroxyalkanoate, wherein the alkyl hydroxyalkanoate fraction is recovered from the second fraction. The separation into the first fraction and the second fraction may be carried out using fractional distillation.

In a second aspect, the distillation step comprises a first step to provide a first fraction enriched in water and mono-alcohol and a second fraction, which may be in the form of distillate bottoms, enriched in alkyl hydroxyalkanoate and saccharide, and a second step to fractionate the second fraction into a saccharide enriched fraction and the alkyl hydroxyalkanoate fraction. This second step may be carried out utilizing an evaporator. The evaporator may be a forced circulation evaporator, a boiling tube evaporator ("BTE"), a wiped film evaporator ("WFE"), a rising film evaporator, or a climbing evaporator.

In a third aspect, the distillation step comprises a first step to provide a first fraction enriched in water, mono-alcohol, and alkyl hydroxyalkanoate, and a second fraction, which may be in the form of distillate bottoms, enriched in saccharide. Further, this embodiment comprises a second step to fractionate the first fraction into a water and mono-alcohol enriched fraction and the alkyl hydroxyalkanoate fraction. This second step may be carried out utilizing fractional distillation or an evaporator. The evaporator may be a forced circulation evaporator, a boiling tube evaporator, a wiped film evaporator, a rising film evaporator, or a climbing evaporator.

In the distillation processes described above, a reduced pressure typically below atmospheric pressure is used to recover the alkyl hydroxyalkanoate fraction. In certain aspects, the pressure of the distillation step may range from 0.1 torr to 750 torr, 0.1 torr to 200 torr, 0.1 torr to 100 torr, and more specifically 0.5 torr to 100 torr.

It is desirable to carry out the distillation process under high vacuum conditions to minimize contact time and temperature, which consequently minimizes undesirable interfering reactions. In the various aspects, the maximum temperature in which to operate distillation is typically 160° C. at atmospheric pressure, which consequently minimizes the distillation of higher molecular weight organic acid esters, for example, esters of succinic acid.

In certain aspects, the reaction product typically has a composition comprising less than 3% by weight of high molecular weight organic acid esters, and more preferably less than 2% by weight percent of high molecular weight organic acid esters, and even more preferably less than 1% by weight of high molecular weight organic acid esters as it progresses through the series of distillation steps.

Percent Yield & Percent Recovery

For all embodiments, the percent yield is typically greater than 50%, for example, greater than 60%, greater than 70%, greater than 80%, greater than 90%, and more preferably greater than 95%. The percent recovery is typically greater than 50%, for example, greater than 60%, greater than 70%, greater than 80%, greater than 90%, and, more preferably greater than 95%.

Methods

The following methods described further below are used in the various examples and are presented to illustrate the present invention and to assist one of ordinary skill in making and using the same. The methods are not intended in any way to otherwise limit the scope of the invention.

Method for Calculating Free Alkanoates and Alkanoate Equivalents

The free hydroxyalkanoate and total hydroxyalkanaote content in hydroxyalkanoate containing compositions is determined by a titration method similar to the method described in the Holten reference above. "Bound" hydroxyalkanoate is the hydroxyalkanoate that is in the form of esters and is calculated as shown below. Hydroxyalkanoate equivalents can then be calculated from the free and bound hydroxyalkanoates.

Free hydroxyalkanoate=$J$% by weight ($J$ is similar to the free acidity, i.e., $a$, in the Holten reference)

Total hydroxyalkanoate=$K$% by weight ($K$ is similar to the total lactic acid, i.e., $a+b$, in the Holten reference)

Bound hydroxyalkanoate=$(K-J)$% by weight

Hydroxyalkanoate Equivalents=$J+[(K-J)\times C]$ % (where "$C$" for 3 carbon hydroxyalkanoates is 90/72; where "$C$" for 4 carbon hydroxyalkanoates is 104/86; where "$C$" for 5 carbon hydroxyalkanoates 118/100)

Ultra Performance Liquid Chromatography (UPLC) Method for the Analysis of Ethyl Lactate:

This method is used to analyze the content of ethyl lactate in reaction mixtures. The UPLC method consists of the following steps:

Sample prep: An aliquot of approximately 128 mg (+/−5 mg) of sample is added to a graduated 15 mL polypropylene centrifuge tube, using a volumetric pipette, with 1 mL internal standard (I.S.). The internal standard is methyl lactate in acetonitrile at a concentration of 55 mg/ml. The sample is brought to the 5 mL mark with acetonitrile, capped tightly, and vortexed for 30 seconds followed by sonication for 3 minutes. After sonication, the sample is centrifuged for 3 minutes at 5000 RPM using a microcentrifuge, then 200 microliters (µL) of the supernatant is transferred to a limited volume LC vial and subject to UPLC-UV (210 nm) analysis, as explained in Step (2) below. The final concentration of the internal standard in the sample is approximately 11 mg/mL. The pressure used for this method ranges from 8000 to 10000 psi.

Chromatographic separation: For this step, a Waters UPLC is used along with Waters Acquity HSS T3 C18, 2.1 mm×100 mm, 1.8 um analytical column. The column is maintained at 40° C. A mobile phase gradient is used where mobile phase A is 0.1% formic acid and mobile phase B is acetonitrile, the phase gradient is outlined in Table 1. The retention time for ethyl lactate is 4.67 minutes, and the retention time for methyl lactate (IS) is 3.02 minutes. Injection volume of 1 µL is used and the detection is done with a Waters Acquity PDA detector.

TABLE 1

| Time (min) | Flow Rate (mL/min) | % A | % B |
|---|---|---|---|
| Initial | 0.52 | 100.0 | 0.0 |
| 1.00 | 0.52 | 100.0 | 0.0 |
| 3.80 | 0.52 | 92.5 | 7.5 |
| 4.70 | 0.52 | 92.5 | 7.5 |
| 5.20 | 0.52 | 90.0 | 10.0 |
| 5.60 | 0.57 | 5.0 | 95.0 |
| 7.00 | 0.62 | 5.0 | 95.0 |
| 7.10 | 0.62 | 100.0 | 0.0 |
| 8.70 | 0.62 | 100.0 | 0.0 |
| 9.00 | 0.52 | 100.0 | 0.0 |

Ultra High Performance Liquid Chromatography (UHPLC) Method for the Analysis of Ethyl 3-Hydroxypriopionate:

This method is used to analyze the content of ethyl 3-hydroxypropionate in reaction mixtures. Approximately 1 gram of sample is weighed into a 50 mL volumetric flask. The analyte is extracted with 50 ml acetonitrile by sonication for 5 minutes. The solution is transferred to a 50 mL centrifuge tube and centrifuged at 3000 rpm for 3 minutes. The supernatant is removed for analysis via UHPLC as follows:

Chromatographic separation: 1 µL of the extraction solution is injected onto either a Waters Acquity UPLC or Agilent 1290 UHPLC. Separation of analytes is performed on a Waters Acquity HSS T3 C18, 2.1 mm×100 mm, 1.8 µm analytical column. The column is maintained at 30° C. A mobile phase gradient is used where mobile phase A is 0.1% formic acid and mobile phase B is acetonitrile, the phase gradient is outlined in Table 2. The retention time for ethyl 3-HP is 2.2 minutes. Quantification of ethyl 3-HP is performed by applying the peak area of the test sample directly to areas for a set of standards measured by UV at 210 nm.

TABLE 2

| Time (min) | Flow Rate (mL/min) | % A | % B |
|---|---|---|---|
| Initial | 0.6 | 97.0 | 3.0 |
| 0.5 | 0.6 | 97.0 | 3.0 |
| 2.5 | 0.6 | 82.0 | 18.0 |
| 3.0 | 0.6 | 5.0 | 95.0 |
| 3.5 | 0.6 | 5.0 | 95.0 |
| 4.0 | 0.6 | 97.0 | 3.0 |
| 5.5 | 0.6 | 97.0 | 3.0 |

GC Method 1: Measuring Ethyl Lactate Concentration in Distilled Fractions Using GC-FID Method:

An Agilent 7890 Gas Chromatograph with a flame ionization detector is used to measure the purity of ethyl lactate in the distilled samples. A Hewlett Packard HP-5 column (length=25 m, i.d.=0.2 mm, film=0.5 mm) is used. The run profile is: 50° C. initial, hold 4.4 min, 30° C./min to 200° C., hold 2.6 min, and then 30° C./min to 250° C., hold 2.6 min. The run time is 16.27 minutes. The inlet temperature is 250° C., the carrier gas is hydrogen, with a flow rate of 0.5 mL/min, and detector temperature of 300° C. The FID makeup is: Nitrogen (30 mL/min); FID Fuel: Hydrogen (40 mL/min); FID Oxidizer: Air (350 mL/min).

100 µL of a distillate sample is placed in a culture tube, and 5 mL of acetonitrile (GC grade) is added. The tube is capped and mixed thoroughly. 1.5 mL of this solution is transferred to a 2 mL GC vial, which is sealed by crimping on a Teflon-lined cap. Injection Volume=1.0 µL. The concentration of ethyl lactate is based on integration of the ethyl lactate peak in the chromatogram relative to all the other peaks, while ignoring the solvent peak (acetonitrile). The retention time for ethyl lactate is 7.1 min.

It shall be understood that this method is the preferred method for measuring ethyl lactate concentrations less than about 95% and is the method used in the relevant claim recitations.

GC Method 2: GC Analysis of Ethyl Lactate and Ethanol in Reaction Mixtures

The GC instrument is an Agilent 7890 Gas Chromatograph with split/splitless injector and flame ionization detector. The column is an Agilent HP-5 column (length=25 m, i.d.=0.2 mm, film=0.5 µm). Initial oven temperature was 50° C., held for 3.0 min, then a 15° C./min ramp up to 325° C., and held there for 8.67 min, for a total run time of 30 min. Inlet Temperature at 275° C., with Hydrogen as the carrier gas at a constant flow of 0.5 mL/min. The FID detector temperature was 275° C., with Hydrogen (40 mL/min) as the fuel.

100 mg of the test material was diluted with 5 mL of GC grade Acetonitrile in a culture tube. The tube was capped and mixed thoroughly by sonication. Filtered 1.5 mL of the solution through a 0.2 µm filter, and transferred to a GC vial with a Teflon-lined cap. Sample injection volume was 1.0 µL.

The retention times of ethanol and ethyl lactate were approximately 2.16 min and 6.56 min respectively. The concentrations of ethanol and ethyl lactate in the reaction mixtures were determined based on peak intensities compared with individual standard curves generated with high purity ethanol and ethyl lactate.

It shall be understood that this method is used to determine ethyl lactate concentration in certain examples, but is not the preferred method of determining ethyl lactate.

GC Method 3: GC Analysis of High Concentrations of Ethyl Lactate

The GC instrument, column, program etc. are identical to GC Method 2 above. The only difference was the sample was injected into the GC without dilution in a solvent. Approximately 1 mL of sample was placed in a GC vial containing a Teflon-lined cap, and 0.2 µL was injected. The % area of ethyl lactate relative to all the other components, minus peaks from the solvent, was reported as the purity of ethyl lactate. It shall be understood that this method is the preferred method for measuring ethyl lactate concentrations greater than and equal 95% and is the method used in the relevant claim recitations.

Method for Determining APHA Color

APHA color, also referred to as the Hazen scale, and more appropriately as the Platinum Cobalt (Pt/Co) scale, is a color standard named for the American Public Health Association and defined by ASTM D1209.

EXAMPLES

The following examples are presented to illustrate the present invention and to assist one of ordinary skill in making and using the same. The examples are not intended in any way to otherwise limit the scope of the invention.

Note, for all tables that refer to moisture percent it shall be understood that moisture percent refers to water content/percent.

Example 1: Production of Ethyl Lactate Using Recovery Bottoms 50.42 grams of recovery bottom sample from a lactic acid process, having a composition as detailed in Table 3, is mixed with 50.42 grams of ethanol (200 proof). To this first mixture, 1% by weight relative to the recovery bottom of 98% sulfuric acid is added as the catalyst to form the reaction mixture. The reaction mixture is constantly stirred and is heated to a temperature of 78-80° C. and is carried out at atmospheric pressure. The reaction mixture is held at this temperature for 5 hours, after which the reaction mixture contains 24.72 grams of ethyl lactate. This equates to a percent yield of 52.5%. The ethyl lactate in the reaction mixture is measured using the UPLC method.

TABLE 3

| Compound | Weight Percent (wt %) |
|---|---|
| Lactic Acid Equivalents (i.e., lactate equivalents) | 71.23 wt % |
| Free lactic acid (i.e., free lactate) | <1 wt % |
| Saccharide Equivalents | 11.1 wt % |
| Water | <1 wt % |

Example 2: Production of Ethyl Lactate Using Recovery Bottoms 52.8 grams of recovery bottom sample from a lactic acid process, having a composition as detailed in Table 3, is mixed with 52.8 grams of ethanol (200 proof). To this first mixture, 1% by weight relative to the recovery bottom of 35% aqueous hydrochloric acid is added as the catalyst to form the reaction mixture. The reaction mixture is constantly stirred and is heated to a temperature of 78-80° C. and is carried out at atmospheric pressure. The reaction mixture is held at this temperature for 5 hours, after which the reaction mixture contains 24.33 grams of ethyl lactate. This equates to a percent yield of 49.6%. The ethyl lactate in the reaction mixture is measured using the UPLC method.

Example 3: Production of Ethyl Lactate Using Recovery Bottoms 54.3 grams of recovery bottom sample from a lactic acid process, having a composition as detailed in Table 3, is mixed with 54.3 grams of ethanol (200 proof). To this first mixture, 1% by weight sodium hydroxide relative to the recovery bottom is added as the catalyst to form the reaction mixture. The reaction mixture is constantly stirred and is heated to a temperature of 78-80° C. and is carried out at atmospheric pressure. The reaction mixture is held at this temperature for 5 hours, after which the reaction mixture contains 5.41 grams of ethyl lactate. This equates to a percent yield of 10.7%. The ethyl lactate in the reaction mixture is measured using the UPLC method.

Example 4: Production and Distillation of Ethyl Lactate Using Recovery Bottoms 125.3 grams of recovery bottoms sample from a lactic acid process, having a composition as detailed in Table 3, is mixed with 125.3 grams of ethanol (200 proof). To this first mixture, 2% by weight relative to the recovery bottom of 98% sulfuric acid is added as the catalyst to form the reaction mixture. The reaction mixture is constantly stirred and is heated to a temperature of 78-80° C. and is carried out at atmospheric pressure. The reaction is carried out for 10 hours at which point the reaction mixture contains 86.42 grams of ethyl lactate. This equates to a percent yield of 73.8%. The ethyl lactate in the reaction mixture is measured using the UPLC method.

The reaction mixture is neutralized with sodium ethoxide to a pH of 7. 209 grams of this neutralized reaction product is used as a feed for the distillation process. Fractional distillation experiments are carried out in batch scale distillation in a flask at 100 torr. Table 4 shows the conditions under which six fractions are collected and the concentration of ethyl lactate in each fraction is determined using the GC-FID method (GC Method 1), as described above. The total amount of ethyl lactate recovered in these fractions equates to 100 percent recovery by distillation. The overall yield for the process is 73.8%. Although the recovery does not appear high in certain fractions, one skilled in the art would understand that an increased number of theoretical stages/plates in a commercial setup will provide high percent recovery and high purity. For example, typically greater than 80 percent recovery, typically 90 percent recovery, and in some instances greater than 92 percent recovery; and, with greater than 90% purity, for example, 95% purity, typically 98% purity, in some instances greater than 99% purity.

TABLE 4

| Sample I.D. | | Feed | Frac. 1 | Frac. 2 | Frac. 3 | Frac. 4 | Frac. 5 | Frac. 6 |
|---|---|---|---|---|---|---|---|---|
| Ethyl Lactate wt in feed and each fraction | grams | 57.3 | 0 | 0.5 | 3.8 | 13.1 | 24.9 | 15.1 |
| Ethyl Lactate Purity in feed and each fraction | wt % | 27.40 | 0.00 | 3.20 | 11.50 | 44.70 | 80.40 | 76.40 |
| Temperature | ° C. | — | 34 | 39 | 46 | 108 | 136 | 160 |
| Pressure (absolute) | Torr | | 100 | 100 | 100 | 100 | 100 | 100 |

Example 5: Production and Distillation of Ethyl Lactate Using Recovery Bottoms Experiments may be carried out using a 50 L jacketed reactor. First, 17.7 kilograms ethanol is added to the reactor and heated to 50° C. by passing hot water through the reactor jacket. The hot water is circulated using a hot water bath. 17.7 kilograms of recovery bottom sample from a lactic acid process, the composition of which is specified in Table 3, is preheated to 78-80° C. and added to the reactor. To this first mixture, 2% by weight relative to the recovery bottom of 98% sulfuric acid is added as the catalyst. The reaction is carried out for 6 hours at 78-80° C. and at atmospheric pressure to form the reaction product. A sample of the reaction mixture is taken from the reactor and ethyl lactate concentration is determined using the UPLC method. The reaction mixture has 12.94 kilograms of ethyl lactate which equates to a percent yield of 78.34%. The synthesized ethyl lactate is subsequently neutralized using sodium ethoxide and the neutralized reaction mixture is used as a feed for the distillation.

Distillation experiments are carried out with laboratory pilot scale rotovap (Buchi Rotovapor R-153) with a provision for continuous feed using 39.64 kilograms of neutralized reaction product. This setup has the capability to measure the inline vapor temperature along with the bath temperature. Three different distillate fractions are collected and the concentration of ethyl lactate in each fraction determined using the GC-FID method (GC Method 1), as illustrated in Table 5. The first fraction is ethanol with 0 wt % ethyl lactate, the second fraction contains 58.63 wt % of ethyl lactate, and the third fraction contains 96.88 wt % ethyl lactate concentration with 0.9 wt % moisture and an acid value of 750 ppm. The percent recovery is 67.5% and the overall recovery is 52.8%.

As demonstrated in Table 5, reduced pressures, for example below 30 Torr (Fraction 3), improve the purity of the ethyl lactate.

TABLE 5

| Sample I.D. | | Feed | Frac. 1 | Frac. 2 | Frac. 3 |
|---|---|---|---|---|---|
| Ethyl Lactate purity in feed and each fraction | wt % | 30.10 | — | 58.63 | 96.88 |

TABLE 5-continued

| Sample I.D. | | Feed | Frac. 1 | Frac. 2 | Frac. 3 |
|---|---|---|---|---|---|
| Ethyl Lactate wt in feed and each fraction | Kg | 11.93 | — | 4.46 | 3.6 |
| Bath Temp. | ° C. | — | 62 | 75 | 97 |
| Vapor Temp. | ° C. | — | 47 | 62 | 57 |
| Pressure (absolute) | Torr | — | 90 | 32 | 17 |

Further, distillation is carried out of the second fraction of the first distilled product which contains 58.63 wt % of ethyl lactate concentration. In the second distillation, again three fractions are collected, and are summarized in Table 6.

TABLE 6

| Sample I.D. | | Feed | Frac. 1 | Frac. 2 | Frac. 3 |
|---|---|---|---|---|---|
| Ethyl lactate purity in feed and each fraction | wt % | 58.63 | — | 54.22 | 99.68 |
| Bath Temp. | ° C. | — | 32 | 70 | 80 |
| Vapor Temp. | ° C. | — | 32 | 65 | 72 |
| Pressure (absolute) | Torr | — | 42 | 42 | 42 |

As illustrated in Table 6, the third fraction contains 99.68 wt % ethyl lactate concentration with 0.07 wt % moisture and an acid value of 550 ppm, demonstrating that a series of distillation steps of a specific fraction can further improve ethyl lactate purity.

Example 6: Effect of pH on Ethyl Lactate Recovery

Reaction is carried out in a 2 L round bottom glass flask by mixing lactic acid solids (BTE bottoms) and ethanol. The round bottom flask is attached to a vertical glass condenser which is cooled with 5-7° C. water. The total reaction mixture weighs approximately 1500 gm with a mass ratio of 60:40 ethanol to lactic acid solids. The added ethanol is in molar excess to drive the reaction towards formation of ethyl lactate. The mixture is heated to 72-75° C. At this point 1.54% of 93% sulfuric acid is added to the reaction mix and the reaction is further heated to 80-83° C. and maintained at this temperature for 8 hours. The reaction is cooled to 23-25° C. and is divided into 3 aliquots each weighing approximately 300 grams. One of these aliquots is neutralized with 50% sodium hydroxide to pH 4, second aliquot is neutralized to pH 5 with 50% sodium hydroxide and the third aliquot is was neutralized to pH 6 with 50% sodium hydroxide.

Each of these neutralized aliquots is processed in a glass distillation set-up in a batch mode to recover the volatile components namely ethanol, water and ethyl lactate as an overhead distillate. The ethyl lactate in the distillate and bottom residue is measured using GC Method 2. The distillation conditions are in Table 7.

TABLE 7

| Tray or packing | None |
|---|---|
| Max Reboiler Temp (° C.) | 137.3-145 |
| Max Vacuum (Torr) | 7 |
| Condenser Temp (° C.) | 2 |
| Vapor Temp (° C.) | 66.9-67.2 |

The results of the distillation trial are tabulated in Table 8, Table 9, and Table 10.

TABLE 8

| pH 6 | Feed Composition | | Residue Composition | | Distillate Composition | | Cold Trap Composition | | |
|---|---|---|---|---|---|---|---|---|---|
| Component | % | (grams) | % | (grams) | % | (grams) | % | (grams) | % Recovered |
| Total Mass | N/A | 314.19 | N/A | 90.19 | N/A | 215.16 | N/A | 0 | 97.19 |
| Ethyl Lactate | 31.68 | 99.53 | 5.65 | 5.10 | 42.12 | 90.63 | 0.00 | 0.00 | 96.17 |

TABLE 9

| pH 5 | Feed Composition | | Residue Composition | | Distillate Composition | | Cold Trap Composition | | |
|---|---|---|---|---|---|---|---|---|---|
| Component | % | (grams) | % | (grams) | % | (grams) | % | (grams) | % Recovered |
| Total Mass | N/A | 311.75 | N/A | 94.95 | N/A | 214.98 | N/A | 0.34 | 99.53 |
| Ethyl Lactate | 30.62 | 95.46 | 2.88 | 2.73 | 42.22 | 90.76 | 1.20 | 0.00 | 97.94 |

TABLE 10

| pH 4 | Feed Composition | | Residue Composition | | Distillate Composition | | Cold Trap Composition | | |
|---|---|---|---|---|---|---|---|---|---|
| Component | % | (grams) | % | (grams) | % | (grams) | % | (grams) | % Recovered |
| Total Mass | N/A | 301.32 | N/A | 86.73 | N/A | 211.96 | N/A | 0.56 | 99.31 |
| Ethyl Lactate | 34.02 | 102.50 | 2.32 | 2.01 | 45.53 | 96.51 | 3.44 | 0.02 | 96.14 |

As illustrated in the tables, ethyl lactate recovery remains high at pH ranges of 4, 5, and 6. Thus, as stated above, a neutralization to a pH of 7 is not required which can provide cost savings (as it minimizes the amount of base used and process time necessary to raise the pH) and minimizes the water content.

Example 7: Distillation Configuration #1

Refer to FIG. 1 for an illustration of the block diagram for this configuration. First, a stirred tank jacketed reactor or a tubular flow reactor is used to react lactic acid recovery bottoms and ethanol in the presence of a sulfuric acid catalyst. Sodium hydroxide is added to the reactant before entering a first distillation step. The first distillation is a wiped film evaporator unit in which the volatile components comprising ethanol, water and ethyl lactate are recovered as a distillate. The non-volatile components are taken out as the bottom residue stream. The distillate from the first distillation step enters a second distillation step. The second distillation step is a fractional distillation using a packed or tray column, and preferably a packed column. In this set-up, the ethanol-water mix is collected as a distillate, while the product of interest, ethyl lactate, is collected as the bottom product. Considering that ethyl lactate forms the bottoms stream, it is challenging to achieve high purity ethyl lactate because minor impurities such as color bodies remain in the bottoms stream. This issue may be overcome by including an additional distillation unit in which the bottom product from the second distillation step is fed to an additional distillation unit and ethyl lactate is recovered as a distillate product.

Example 8: Sample Distillation Configuration #2

Refer to FIG. 2 for an illustration of the block diagram for this configuration. First, a stirred tank jacketed reactor or a tubular flow reactor is used to react lactic acid recovery bottoms and ethanol in the presence of a sulfuric acid catalyst. Sodium hydroxide is added to the reactant before entering a first distillation step. The first distillation is a fractional distillation using a packed or tray column, and preferably a hybrid column with a tray in the bottoms section and packing in the top section of the distillation column. Ethanol and water are taken off as the distillate, and the bottoms move on to a second distillation step, which utilizes a wiped film evaporator with an attached column to recover ethyl lactate as a distillate. The wiped film evaporator acts like a reboiler and column and thus achieves a higher purity of ethyl lactate (in the distillate) when compared against Example 7. The advantage of this configuration is that since ethyl lactate is recovered as the distillate, minor impurities such as the color bodies remain in the bottoms.

Whereas the ethyl lactate in Distillation Configuration 1 has a yellow color, three experiments utilizing Distillation Configuration 2 produced ethyl lactate with APHA colors around 10 or below, as demonstrated in Table 11.

TABLE 11

|  | Target | Lot A | Lot B | Lot C |
| --- | --- | --- | --- | --- |
| Ethyl lactate Purity (%) - GC |  | 98.39% | 98.81% | 98.24% |
| Color (APHA) | 10 max | 8.6 | 10.1 | 9.3 |

Example 9: Synthesis of Ethyl Lactate from Lactic Acid Recovery Bottoms ("BTE Bottoms") Under Pressure with and without a Catalyst A high temperature oven was heated to the desired temperature (see below 150, 175, 200, or 220° C.). Six 600 mL beakers were filled halfway with silica and placed in the oven to acclimate to the temperature. Six 1" stainless steel Swagelok assemblies (part #OMA-CARLAB-003-0) were cleaned and dried. Both ends of each assembly were Teflon taped and Silver Goop® Thread Lubricant Oil-Based Swagelok (part #MS-TL-SGT) was used around the threads on top of the Teflon tape and on the threads of the caps, then one end of each assembly was capped and secured.

The reaction mixture was 60:40 or 40:60 (w/w) as indicated below of Ethanol (Cargill, purity >99%) to BTE bottoms. The reaction mixture (250 g) was prepared in a 250 ml bottle and allowed to mix in a sonicator until the mixture was homogeneous. Then 25 grams of reaction mixture was transferred into six 40 ml glass vials. The contents of the vials were transferred into the six Swagelok assemblies, then capped and secured. The capacity of the assembly is approximately 50 ml. Excessive tightening was essential to ensure a proper seal at the desired temperature.

The beakers were carefully removed from the oven and each Swagelok assembly was wedged into its own beaker of silica so that the bottoms cap was covered. The six beaker assembly combinations were then placed back in the oven. Every 45 minutes one beaker assembly combination was removed from the oven and the assembly was taken out of the silica to cool in front of a fan. When the assembly was cool the contents were transferred to a 40 ml glass vial to be analyzed via GC. The moisture analysis (Karl Fisher) and pH were also taken for each sample. BTE Bottoms analysis by the titration method mentioned above had the following numbers in Table 12:

TABLE 12

| Free Lactate | 35.95% |
| --- | --- |
| Lactate Equivalents | 79.40% |

Trial 1: Oven Temperature 120° C., 60:40 (w/w) Ethanol to BTE Bottoms, 50 ml glass pressure tubes, Reaction time 15 hrs: (Table 13).

TABLE 13

| Sample | Yield (%) | Moisture (%) |
| --- | --- | --- |
| Rxn 1 | 48.6 | 3.56 |
| Rxn 2 | 49.8 | 3.18 |

Trial 2: Oven Temperature 150 or 175° C., $1^{st}$ set 60:40 and $2^{nd}$ set 40:60 Ethanol to BTE Bottoms, Reaction Time 15 hrs: (Table 14).

TABLE 14

| Sample | Yield (%) | pH | Moisture (%) |
| --- | --- | --- | --- |
| Rxn 1 60:40 150° C. | 59.1 | 2.9 | 3.97 |
| Rxn 2 40:60 150° C. | 58.3 | 2.2 | 5.11 |
| Rxn 3 60:40 175° C. | 64.9 | 2.9 | 3.69 |
| Rxn 4 40:60 175° C. | 59.1 | 2.4 | 5.48 |

Trial 3: Oven Temperature 200° C., 60:40 (w/w) Ethanol to BTE Bottoms: (Table 15).

TABLE 15

| Sample | Yield (%) | pH | Moisture (%) |
|---|---|---|---|
| Rxn 1 45 min | 6.9 | 2.5 | 2.10 |
| Rxn 2 90 min | 40.1 | 2.6 | 3.19 |
| Rxn 3 135 min | 58.4 | 2.2 | 2.72 |
| Rxn 4 180 min | 69.5 | 2.3 | 3.98 |
| Rxn 5 225 min | 72.8 | 2.3 | 4.34 |
| Rxn 6 270 min | 73.7 | 2.4 | 4.32 |

Trial 4: Oven Temperature 220° C., 60:40 (w/w) Ethanol to BTE Bottoms: (Table 16).

TABLE 16

| Sample | Yield (%) | pH | Moisture (%) |
|---|---|---|---|
| Rxn 1 45 min | 7.0 | 2.5 | 2.34 |
| Rxn 2 90 min | 29.4 | 2.7 | 3.33 |
| Rxn 3 135 min | 59.4 | 2.8 | 3.92 |
| Rxn 4 180 min | 71.1 | 2.7 | 4.73 |
| Rxn 5 225 min | 73.5 | 2.8 | 5.01 |
| Rxn 6 270 min | 73.2 | 2.8 | 5.48 |

Trial 5: Oven Temperature 200° C., 60:40 (w/w) Ethanol to BTE Bottoms, 4% water addition based off of the total BTE bottoms mass: (Table 17).

TABLE 17

| Sample | Yield (%) | pH | Moisture (%) |
|---|---|---|---|
| Rxn 1 45 min | 2.9 | — | — |
| Rxn 2 90 min | 19.9 | — | — |
| Rxn 3 135 min | 49.1 | — | — |
| Rxn 4 180 min | 62.5 | — | — |
| Rxn 5 225 min | 66.9 | — | — |
| Rxn 6 270 min | 67.7 | 2.8 | 5.66 |

Trial 6: Oven Temperature 200° C., 60:40 (w/w) Ethanol to BTE Bottoms, 0.2% Sulfuric acid addition based off of the total reaction mixture: (Table 18).

TABLE 18

| Sample | Yield (%) | pH | Moisture (%) |
|---|---|---|---|
| Rxn 1 45 min | 14.8 | — | — |
| Rxn 2 90 min | 40.2 | — | — |
| Rxn 3 135 min | 58.4 | — | — |
| Rxn 4 180 min | 69.4 | — | — |
| Rxn 5 225 min | 74.7 | 1.7 | 4.58 |
| Rxn 6 270 min | 74.7 | 1.7 | 5.32 |

Example 10: Synthesis of Ethyl Lactate from WFE Bottoms

Recovery bottoms sample from the Cargill Lactic Acid process, having a composition as detailed in Table 19 below, is mixed with deionized water at a 1.05 molar ratio of water to the ester bonds in the bound lactic acid. 93% sulfuric acid at 1% by weight relative to the total reaction mass is added as the catalyst to the reaction mixture. The reaction mixture is constantly stirred and heated to a temperature of 100° C. under atmospheric pressure for 8 hours. It is believed that free lactic is at least about 20%. The reaction mixture is then mixed with ethanol (Cargill. purity >99%) at the mass ratio of 70:30 of ethanol to reaction mixture. 93% sulfuric acid at 1.44% by weight relative to the total reaction mass is added as the catalyst to the reaction mixture. The reaction mixture is constantly stirred and heated to a temperature of 80-83° C. under atmospheric pressure. The reaction mixture is held at this temperature for 8 hours, and samples are withdrawn at 6 hr and 8 hr for analysis. The total mass is then neutralized with 50% aqueous NaOH to a pH of 4.0 and sampled. The ethyl lactate and moisture content in the collected samples are analyzed via GC and Karl Fisher respectively. The results of the reactions are provided in Table 20, Table 21, and Table 22.

TABLE 19

| Free lactate | 11.72% |
|---|---|
| Lactate Equivalents | 64.70% |

TABLE 20

| | | Mass (g) | |
|---|---|---|---|
| Reaction Step | Components | Rxn 1 | Rxn 2 |
| Hydrolysis | WFE Bottoms | 350.94 | 351.19 |
| | Water | 39.01 | 39.08 |
| | 93% Sulfuric Acid | 4.20 | 4.23 |
| Ester Formation | Ethanol | 920.03 | 921.07 |
| | 93% Sulfuric Acid | 20.26 | 20.46 |
| Neutralization | NaOH | 22.92 | 22.98 |

TABLE 21

Reaction 1

| Sample | Moisture (%) | Ethyl Lactate (% in Rxn Mixture) | Yield (%) |
|---|---|---|---|
| 6 hr | 4.07 | 16.65 | 74.3 |
| 8 hr | 3.82 | 16.63 | 73.6 |
| Neutralized | 4.82 | 15.41 | 68.6 |

TABLE 22

Reaction 2

| Sample | Moisture (%) | Ethyl Lactate (% in Rxn Mixture) | Yield (%) |
|---|---|---|---|
| 6 hr | 4.01 | 16.26 | 72.5 |
| 8 hr | 3.84 | 17.21 | 76.0 |
| Neutralized | 4.87 | 16.42 | 73.0 |

Recovery bottoms sample from the Cargill Lactic Acid process, having a composition as detailed in Table 19 above is mixed with deionized water at a 0.8 molar ratio of water to the ester bonds in the bound lactic acid. The rest of the reaction is procedurally identical to the above reactions. The results of this reaction are provided in Table 23 and Table 24.

TABLE 23

| Reaction Step | Components | Mass (g) Rxn 3 |
|---|---|---|
| Hydrolysis | WFE Bottoms | 352.05 |
| | Water | 29.90 |
| | 93% Sulfuric Acid | 4.19 |

TABLE 23-continued

| Reaction Step | Components | Mass (g) Rxn 3 |
|---|---|---|
| Ester Formation | Ethanol | 902.69 |
|  | 93% Sulfuric Acid | 19.89 |
| Neutralization | NaOH | 22.29 |

TABLE 24

Reaction 3

| Sample | Moisture (%) | Ethyl Lactate (% in Rxn Mixture) | Yield (%) |
|---|---|---|---|
| 6 hr | 3.29 | 17.32 | 75.5 |
| 8 hr | 3.20 | 17.50 | 75.5 |
| Neutralized | 4.65 | 15.96 | 69.3 |

An example similar to Example 10 is carried out (utilizing the similar recovery bottoms and reaction conditions) except deionized water is not added resulting in a percent yield of approximately 30%, i.e., at least doubling the percent yield compared to when deionized water is added. This shows that in some instances increasing the free alkanoate to at least 20% can increase the percent yield and overall recovery. Alternatively, higher temperature and higher pressure could be utilized to obtain higher percent yield and overall recovery.

Example 11: Reaction of 3-Hydroxypropionic Acid Recovery Bottoms ("3-HPRB") with Ethanol ("EtOH")

Recovery bottoms from a 3-Hydroxypropionic acid (3-HP) manufacturing process that utilizes a distillation process for recovering 3-HP are obtained having a composition as detailed in the Table 25 below are mixed with ethanol (200 proof) at mass ratios of 50:50, 40:60 or 30:70 of 3-HPRB to ethanol. 98% sulfuric acid at 1 to 4% by weight relative to the 3-HPRB is added as the catalyst to the reaction mixture. The reaction mixture is constantly stirred and heated to a temperature of 78-80° C. under atmospheric pressure. The reaction mixture is held at this temperature for 6 to 14 hours, after which it is cooled to room temperature and analyzed by UHPLC. The composition of the resulting product is detailed in Table 26.

TABLE 25

| Compound | Weight Percent (wt %) |
|---|---|
| 3-HP Equivalents | 66.74 wt % |
| Free 3-HP | 11.53 wt % |
| Saccharide Equivalents | >1 wt % |
| Water | >0.1 wt % |

TABLE 26

| Reaction mixture (Mass ratio) | Reaction time (hrs) | Total weight of reaction mixture (g) | Yield of 3-HP ethyl ester (%) |
|---|---|---|---|
| 3-HPRB:EtOH (50:50)-6 hr., 1% H2SO4 | 6 | 108.47 | 56.14 |
| 3-HPRB:EtOH (50:50)-6 hr., 2% H2SO4 | 6 | 112.95 | 52.97 |
| 3-HPRB:EtOH (50:50)-6 hr., 3% H2SO4 | 6 | 103.85 | 50.81 |
| 3-HPRB:EtOH (50:50)-6 hr., 4% H2SO4 | 6 | 99.62 | 48.38 |
| 3-HPRB:EtOH (50:50)-6 Hr., 3% H2SO4 | 6 | 113.60 | 51.74 |
| 3-HPRB:EtOH (40:60)-6 Hr., 3% H2SO4 | 6 | 112.65 | 60.54 |
| 3-HPRB:EtOH (30:70)-6 Hr., 3% H2SO4 | 6 | 106.73 | 66.75 |
| 3-HPRB:EtOH (30:70)-8 Hr., 3% H2SO4 | 8 | 112.37 | 66.34 |
| 3-HPRB:EtOH (30:70)-10 Hr., 3% H2SO4 | 10 | 122.33 | 67.24 |
| 3-HPRB:EtOH (30:70)-14 Hr., 3% H2SO4 | 14 | 112.44 | 65.12 |

The results in Table 26 show that no large differences in yield are observed with an increase in catalyst concentration. Further, increasing the ethanol content relative to the 3-HP distillation bottoms from 50:50 to 70:30 increases the yield of 3-HP ethyl ester and increasing the time of the reaction beyond 6 hours at 3-HP distillation bottoms to ethanol ratio of 3:7 did not increase the yield. i.e., the reaction appears to reach equilibrium in about 6 hours.

We claim:

1. A method for producing ethyl 3-hydroxypropionate, comprising:
   a) obtaining a 3-hydroxypropionate containing composition derived from 3-hydroxypropionic acid recovery bottom, comprising:
      (i) at least 40 percent by weight 3-hydroxypropionate equivalents;
      (ii) less than 45 percent by weight free 3-hydroxypropionic acid;
      (iii) at least 1 percent by weight saccharide equivalents; and
      (iv) less than 5 percent by weight water;
   b) mixing ethanol in a molar ratio of from about 1.1 to 1.0 to about 10.0 to 1.0 of ethanol to 3-hydroxypropionate equivalents present in the 3-hydroxypropionate containing composition to obtain a first mixture;
   c) heating the first mixture in the presence of a catalyst to form a reaction product;
   d) distilling the reaction product and recovering an ethyl 3-hydroxypropionate fraction comprising:
      (i) at least 90 percent by weight ethyl 3-hydroxypropionate;
      (ii) less than 1 percent by weight 3-hydroxypropionic acid;
      (iii) less than 1 percent by weight water; and
      (iv) less than 0.5 percent by weight saccharide equivalents.

2. The method of claim 1, wherein step (d) further comprises separating the reaction product into a first fraction enriched in the ethanol and water, and a second fraction enriched in the ethyl 3-hydroxypropionate, wherein the ethyl 3-hydroxypropionate is recovered from the second fraction.

3. The method claim 1, wherein step (d) comprises fractional distillation.

4. The method of claim 1, wherein step (d) comprises:
a first step to provide a first fraction enriched in water and ethanol and a second fraction enriched in the ethyl 3-hydroxypropionate and the saccharide equivalents; and
a second step to fractionate the second fraction into a saccharide equivalents enriched fraction, and an ethyl 3-hydroxypropionate enriched fraction.

5. The method of claim 4, wherein the second step is carried out utilizing an evaporator.

6. The method of claim 1, wherein step (d) comprises:
a first step to provide a first fraction enriched in water, ethanol, and ethyl 3-hydroxypropionate and a second fraction enriched in saccharide equivalents; and
a second step to fractionate the first fraction into a water and ethanol enriched fraction and the ethyl 3-hydroxypropionate enriched fraction.

7. The method of claim 6, wherein the second step is carried out through fractional distillation.

8. The method of claim 6, wherein the second step is carried out utilizing an evaporator.

9. The method of claim 1, wherein the first mixture is heated to a temperature of from about 50° C. to about 110° C.

10. The method claim 1, wherein the first mixture is heated to a temperature from about a reflux temperature of the first mixture for a given reaction pressure to about 20° C. below the reflux temperature of the first mixture for the given reaction pressure during step (c).

11. The method of claim 1, wherein the first mixture is heated to a temperature from about a reflux temperature of the first mixture for a given reaction pressure to about 10° C. below the reflux temperature of the first mixture for the given reaction pressure during step (c).

12. The method of claim 1, wherein the first mixture is heated to a temperature from about a reflux temperature of the first mixture for a given reaction pressure to about 5° C. below the reflux temperature of the first mixture for the given reaction pressure during step (c).

13. The method of claim 1, wherein the pressure in step (c) ranges from 0 PSIG to 125 PSIG.

14. The method of claim 1, wherein the pressure in step (c) ranges from 50 PSIG to 125 PSIG.

15. The method of claim 1, further comprising step (e) which occurs prior to step (d), and wherein step (e) includes a pH adjustment step.

16. The method of claim 15, wherein the pH of the reaction mixture is adjusted to between 3 and 7.5.

17. The method of claim 1, wherein the 3-hydroxypropionate containing composition comprises at least 5 percent by weight saccharide equivalents.

18. The method of claim 1, wherein the 3-hydroxypropionate containing composition comprises less than 3 percent by weight water.

19. The method of claim 1, wherein the 3-hydroxypropionate containing composition comprises less than 2 percent by weight water.

20. The method of claim 1, wherein the 3-hydroxypropionate containing composition comprises less than 1 percent by weight water.

* * * * *